United States Patent [19]
Winter et al.

[11] Patent Number: 5,965,405
[45] Date of Patent: Oct. 12, 1999

[54] METHOD FOR PRODUCING FV FRAGMENTS IN EUKARYOTIC CELLS

[75] Inventors: Gregory Paul Winter, Cambridge, United Kingdom; Lutz Riechmann, La Jolla, Calif.; Geoffrey Thomas Yarranton, Nr. Reading, United Kingdom; Mark William Bodmer; Raymond John Owens, both of Henley-On-Thames, United Kingdom

[73] Assignee: Celltech Limited, Berkshire, United Kingdom

[21] Appl. No.: 08/165,530

[22] Filed: Dec. 13, 1993

Related U.S. Application Data

[62] Continuation of application No. 07/881,089, May 11, 1992, abandoned, which is a continuation of application No. 07/460,151, filed as application No. PCT/GB89/00399, Apr. 17, 1989, abandoned.

[30]   Foreign Application Priority Data

| Apr. 16, 1988 | [GB] | United Kingdom | ................... 8809050 |
| May 13, 1988 | [GB] | United Kingdom | ................... 8811342 |
| Aug. 26, 1988 | [GB] | United Kingdom | ................... 8820284 |
| Apr. 17, 1989 | [WO] | WIPO | ................... PCT/GB89/00399 |

[51] Int. Cl.$^6$ ........................ A61K 39/395; C07K 16/00; C07K 16/46; C12N 15/13
[52] U.S. Cl. ........................ 435/69.6; 435/69.7; 435/328; 530/387.1; 530/387.3; 424/133.1; 424/134.1
[58] Field of Search .............................. 530/387.1, 387.3; 435/69.1, 69.6, 69.7, 328; 424/133.1, 134.1

[56]   References Cited

U.S. PATENT DOCUMENTS

| 4,642,334 | 2/1987 | Moore et al. ........................... 530/388 |
| 4,853,871 | 8/1989 | Pantoliano et al. . |
| 4,946,778 | 8/1990 | Ladner et al. . |
| 5,091,513 | 2/1992 | Huston et al. ........................ 530/387.1 |

FOREIGN PATENT DOCUMENTS

| WO88/01649 | 3/1988 | WIPO . |
| WO88/03558 | 5/1988 | WIPO . |

OTHER PUBLICATIONS

Nakaki et al., "Enhanced Transcription of the 78,000–Dalton Glucose–Regulated Protein (GRP78) Gene and Association of GRP78 with Immunoglobulin Light Chains in a Nonsecreting B–Cell Myeloma Line (NS–1)", *Molecular and Cellular Biology*, vol. 9, No. 5, May 1989, pp. 2233–2238.

Chang et al., "Glucose –Regulated Protein (GRP94 and GRP78) Genes Share Common Regulatory Domains and Are Coordinately Regulated by Common trans–Acting Factors", *Molecular and Cellular Biology*, vol. 9, No. 5, May 1989, pp. 2153–2162.

Ting et al., "The nucleotide sequence encoding the hamster 78–kDa glucose–regulated protein (GRP78) and its conservation between hamster and rat", *Gene*, 55 (1987) pp. 147–152.

Whittle et al., "Expression in COS cells of a mouse–human chimaeric B72.3 antibody", *Protein Engineering*, vol. 1, No. 6, pp. 499–505, 1987.

Hendershot, L. et al.; "The Role of immunoglobulin Heavy Chain Binding Protein . . . "; *Immunology Today*, vol. 8, No. 4, pp. 111–114, 1987.

Gething, M. et al.; "Expression of Wild–Type And Mutant Forms Of Influenza Hemagglutinin . . . "; *Cell*; vol. 46, pp. 939–950, Sep. 12, 1986.

Verhoyen et al., Bio. Essays 8(2): 74–78 (1988).
Morrison et al. Science vol. 229:1202 1985.
Wood et al. Nature vol. 374:446, 1985.
Rudikoff et al. PNAS. vol. 83 p. 7875 1986.

*Primary Examiner*—Julie Reeves
*Attorney, Agent, or Firm*—Venable; John W. Schneller

[57]   ABSTRACT

Methods for preparing Fv fragments which lack linking polypeptides in eukaryotic cells are provided.

10 Claims, 5 Drawing Sheets

FIG. 1

HuVHYS = reshaped heavy chain variable domain
HuVLLYS = reshaped light chain variable domain
AmpR = ampicillin resistance gene
KanR = Kanamycin resistance gene
Eco-gpt = mycophenolic acid resistance gene
col E1 ori = col E1 origin of replication
enh = enhancer
pro = promoter
Restriction sites: B = BamHI; H= Hind III; E= EcoRI;
S = Sac I

FIG. 2

HINDIII
AAGCTTACTGAGCACACAGGACCTC

M G W S C I I L F L V A T A T
ACCATGGGATGGAGCTGTATCATCCTCTTCTTGGTAGCAACAGCTACAGGTAAGGGCTC

ACAGTAGCAGGCTTGAGGTCTGAGACATATATATGGGTGACAATGACATCCACTTTGCCTT 1                  5                  10
G V H S D I Q M T Q S P S S L S A
TCTCTCCCAGGTGTCCACTCCGACATCCAGATGACCCAGAGCCCAAGCAGCCTGAGCGC

CDR1
         20                                    30
S V G D R V T I T C R │ A S G N I H N Y L │
CAGCGTGGGTGACAGAGTGACCATCACCTGTAGAGCCAGCGGTAACATCCACAACTACCT

```
                                              50  CDR2
A W Y Q Q K P G K A P K L L I Y  Y T T
GGCTTGGTACCAGCAGAAGCCAGGTAAGGCTCCAAAGCTCCTGATCTACTACACCACCAC

70
L A D G V P S R F S G S G S G T D F T F
CCTGGCTGACGGTGTGCCAAGCAGATTCAGCGGTAGCGGTACCGACTTCACCTT

90  CDR3
T I S S L Q P E D I A T Y Y C  Q H F W S
CACCATCAGCAGCCTCCAGCCAGAGGACATCGCCACCTACTACTGCCAGCACTTCTGGAG

108
T P R T  F G Q G T K V E I K R
CACCCCCAAGGACGTTCGGCCAAGGGACCAAGGTGGAAATCAAACGTGAGTAGAATTTAAA

CTTTGCTTCCTCAGTTGGATCC
```

METHOD FOR PRODUCING FV FRAGMENTS IN EUKARYOTIC CELLS

This application is a continuation application Ser. No. 07/881,089, filed May 11, 1992, now abandoned which is a continuation of application Ser. No. 07/460,151, filed Jan. 26, 1990 now abandoned, filed as International App. PCT/GB89/00399 filed Apr. 17, 1988.

The present invention relates to a method for producing recombinant DNA proteins, and in particular to a method for producing antibody Fv fragments by recombinant DNA technology.

In the following description, various publications are referred to. These are indicated by a name and a number in square brackets. The full references to the publications are given in numerical order at the end of the description.

The structure of natural antibody molecules is well known. It comprises four chains, two heavy chains and two light chains, the N-terminal ends of which are aligned. Each chain of the antibody forms a number of domains linked to the other domains by relatively flexible amino acid sequences. The light chains consist of an N-terminal variable domain linked to a C-terminal constant domain. The heavy chain consists of an N-terminal variable domain followed by three or more constant domains. The light and heavy chain variable domains in each pair co-operate to form an antigen binding region.

It has been reported in a few isolated instances that it is possible, by careful proteolytic digestion, to separate the antigen binding (or variable) regions of an antibody, each comprising a light and a heavy chain variable domain, from the remainder. This separated region is generally known as the Fv region. It is also known that isolated heavy or light chain variable domains can dimerise to give pseudo-Fv regions.

It has been suggested that Fv or pseudo-Fv regions (hereinafter collectively referred to as Fv fragments) could be of use as diagnostic or therapeutic agents. For instance, an Fv fragment which has been radiolabelled could be used to locate tumours in the body. An Fv structure to which is linked a cytotoxic agent may be used as a chemotherapeutic agent. It has been conjectured that, since Fv fragments are relatively small compared to whole antibody molecules or Fab or F(ab')$_2$ fragments, they will be able readily to reach their targets, bind in large numbers on the targets, and be cleared rapidly from the patient.

Producing Fv regions by proteolytic cleavage is difficult to achieve, even under laboratory conditions, and could not practically be achieved in an industrial context. It has been proposed by Moore and Zaffaroni [1] that Fv fragments could be produced in microorganisms by use of recombinant DNA technology. However, it has been found that, although a microorganism transformed so that it contains the genetic information necessary to produce an Fv fragment can synthesise the required proteins, it is extremely difficult to obtain active Fv fragments. The synthesised protein is usually found in insoluble inclusions in the microorganism. In order to obtain the Fv fragments, it is necessary to disrupt the microorganism structure, isolate the protein and then renature the protein, as described by Field et al. [2]. However, yields of Fv fragments made by such methods are low.

Skerra and Pluckthun [3] confirm that in general it was believed that it was not possible to produce functional Fv fragments by recombinant DNA technology using bacterial host cells. However, they devised a particular expression system which enabled them to produce a functional anti-phosphoryl-choline Fv fragment in E. Coli. Only small amounts of protein (0.2 mg/l of culture) were produced by this expression system. Thus, it remains to be seen whether the system they have developed can produce commercially viable quantities of product. It also remains to be seen whether the particular expression system can be used to produce Fv fragments derived from other antibodies in other bacterial systems.

It is therefore desirable to be able to produce Fv fragments in good yields by recombinant DNA technology.

According to the present invention, there is provided a method for producing Fv fragments comprising:

transforming a eukaryotic host cell with a eukaryotic expression vector comprising an operon having a DNA sequence which encodes the variable domain only of an antibody light or heavy chain, culturing the transformed host cell under conditions which cause the protein encoded by the DNA sequence to be synthesised; and collecting the synthesised protein.

Preferably, the chains of the Fv fragment are secreted and correctly assembled by the host cell such that fully functional Fv fragments are produced in the culture supernatant.

In one preferred alternative, the host cell is also transformed with a second eukaryotic expression vector comprising an operon having a DNA sequence encoding a complementary heavy or light chain variable domain respectively. In a second preferred alternative, the first expression vector has a second operon comprising a DNA sequence encoding a complementary heavy or light chain variable domain respectively. In either case, the translation product will be an Fv fragment comprising a dimer of a light and a heavy chain variable domain.

If desired, one or both of the variable domains may be expressed as a fusion protein having an effector protein, such as an enzyme, ligand or toxin, fused to its C-terminal end. The effector protein may be used to bind radioactive or fluorescent molecules for imaging, or cytotoxic agents for therapeutic use. In this case, one or both of the operons will include a DNA sequence encoding the effector protein linked in reading frame to the 3' end of the variable domain encoding sequence.

Where the variable domains are translated separately, the Fv fragments produced will be held together only by non-covalent bonding. Thus, the Fv fragment may be susceptible to disassociation, for instance by lowering of pH. In order to improve the stability of the Fv fragment, the DNA coding sequences may be altered towards their 3' end so that one or more cysteine residues are produced towards the C- terminal end of each variable domain. If such an alteration is made, the variable domains in the dimer may become linked together by disulphide bonding. This may also promote assembly of the Fv fragment.

Alternatively, the Fv fragment may be stabilised by use of a vector having in the operon a first DNA sequence encoding a first variable domain and a second DNA sequence encoding a second variable domain, the first and second sequences being linked by a third DNA sequence which encodes a joining peptide sequence. A similar proposal to this is disclosed by Ladner and Bird [4]. The domain encoding sequences may be arranged so that, in the translated product, the first variable domain has its C-terminus linked by the joining peptide sequence to the normal N-terminal of the second variable domain. In this case, the joining peptide sequence will need to be reasonably long and flexible.

The first and second domain encoding sequences may encode the same domain, but preferably encode complementary light and heavy chain domains. In this case, only one effector protein, if desired, could be fused to the Fv fragment.

The DNA coding sequence(s) may comprise cDNA, genomic DNA or mixtures thereof. Preferably, the coding sequence(s) are derived from monoclonal antibodies, advantageously mouse monoclonal antibodies. The coding sequences may be "native" sequences or may be "humanized" sequences wherein the complementarity determining regions (CDRs) from a monoclonal antibody from one species has been grafted onto the framework regions (FRs) from another species. The techniques which can be used for "humanizing" antibodies have been described by Reichmann et al. [5].

According to a second aspect of the invention, there is provided an Fv structure wherein one or both of the domains comprises a fusion protein having the variable domain at its N-terminal end and an enzyme, ligand or toxin at its C-terminal end.

The domain encoding sequences will be under the control of a promoter in the operon. Preferably the promoter is a strong promoter such as the promoter from the human cytomegalovirus (HCMV) major immediate early (MIE) gene.

The eukaryotic host cells to be transformed are preferably mammalian cells, and such cells as CHO cells may be used. However, it is most preferred that the host cells are mammalian myeloid cells, and in particular myeloma cells which, prior to transformation, do not secrete whole antibody or light chains. Such cell lines are well known and widely available.

The techniques by which expression vectors suitable for use in the present invention can be produced and transformed into host cells are well known in the art, and are described, for instance, by Maniatis [6].

The Fv fragment produced by the transformed host cell may be collected by any of the methods currently available. For instance, the antigen may be immobilised on a chromatography medium and the culture supernatant passed over the medium.

This separates the Fv fragment from the remaining constituents of the supernatant.

The present invention also includes eukaryotic expression vectors for use in the method of the present invention, eukaryotic host cells transformed with the vectors and Fv fragments produced by the method of the present invention.

Given the failure to produce easily recoverable quantities of functional Fv structures using recombinant DNA technology in microorganisms (except using the particular expression system of Skerra and Pluckthun [3], it is surprising that Fvs can be produced in eukaryotic cells in good yields as stable products which are secreted into the culture medium. Yields of Fvs of about 10 mg/l of culture have been obtained and improved yields are expected with further development of the eukaryotic expression systems. Thus, the present invention provides the unexpected benefit of being able to produce Fv structures in commercially useful quantities by recombinant DNA technology. Additionally, an advantage of the use of eukaryotic host cells is that the secreted Fv structures are typically produced in the absence of bacterial pyrogens.

A further surprising feature is that the Fv fragment can be assembled properly in the absence of a binding site in the Fv fragment for BIP (heavy chain binding protein). It has been conjectured that binding of BIP is essential to ensure correct assembly of antibody.

It is believed that the process of the present invention will be generally applicable to any Fv fragment and will thus enable the production of Fv fragments having desired specificities in an easy manner. Moreover, since the Fv fragments may be produced in mammalian cells, it will be possible readily to obtain regulatory approval for their use in vivo.

Some embodiments of the present invention are now described, by way of example only, with reference to the accompanying drawings, in which.

EXAMPLE 1

The heavy chain variable domain of antibody D1.3 (a mouse monoclonal antibody specific for lysozyme (Verhoeyen et al.[7]) was "humanised" by grafting the DNA sequences encoding its CDRs onto the DNA sequences encoding the FRs of the monoclonal antibody produced by the human myeloma NEW (Saul et al. [8]). The light chain variable domain of D1.3 was also humanised by grafting the DNA sequences encoding its CDRs onto the DNA sequences encoding the FRs of a human kappa chain concensus sequence (Kabat et al. [9]) similar to the sequence of a Bence Jones protein REI (Epp et al. [10]). The grafting was carried out using site directed mutagenesis with long oligonucleotides according to the procedure of Reichmann et al. [4].

For the expression of an Fv structure, stop codons were introduced at the 3' end of the coding sequences for the humanised light and heavy chain variable domains.

Figure 1:
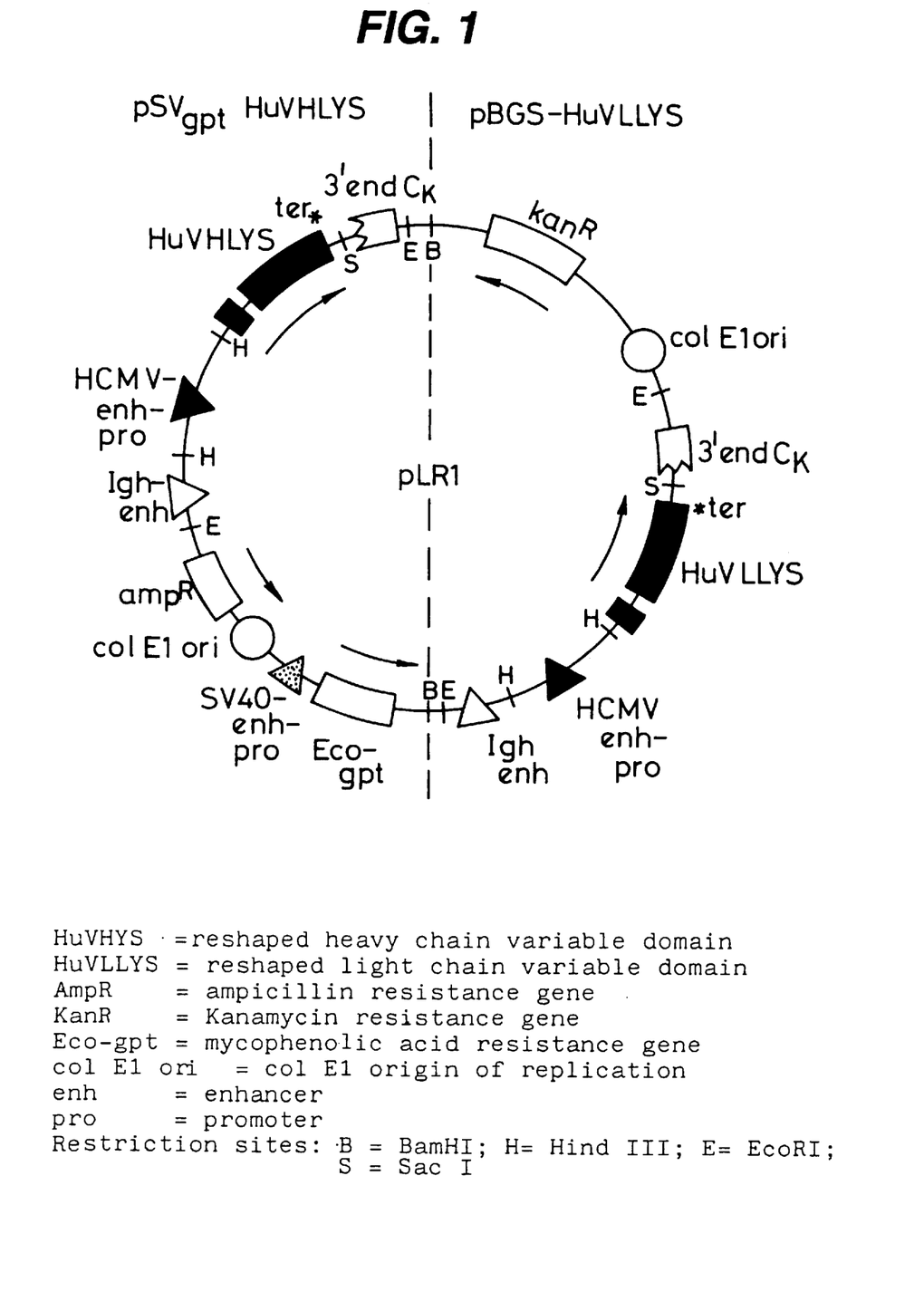
FIG. 1 shows the construction of a vector for use in producing a humanised anti-lysozyme Fv fragment.

In a first construct, the coding sequences were placed in a single vector, but independently under the control of an immunoglobulin heavy chain promoter/enhancer sequence (Verhoeyen et al. [7]). In a second construct, the coding sequences were each placed under the control of the HCMV-MIE gene promoter/enhancer sequence (Stenberg et al. [11] and Boshart et al. [12]). The HCMV-MIE gene promoter/enhancer sequences were fused to the 5' flanking sequences of the signal sequences at the 5' end of the variable domain coding sequences utilizing the RNA start site of the HCMV sequence. The second construct, pLR1, is shown in FIG. 1.

Figure 2:
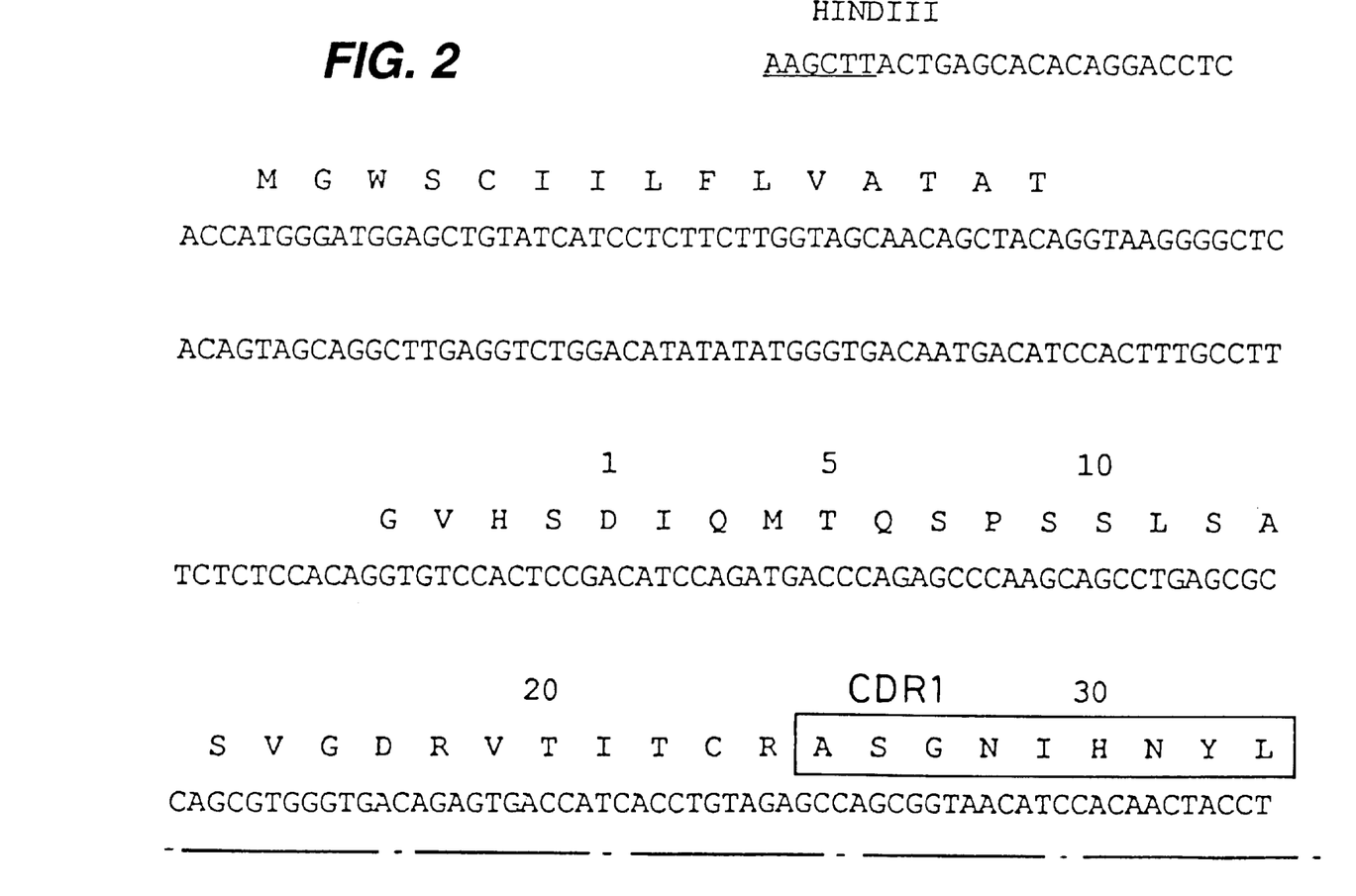
FIG. 2 shows the nucleotide sequence and corresponding amino acid sequence of the reshaped HuVLLYS gene used in the vector of FIG. 1.
Figure 3:
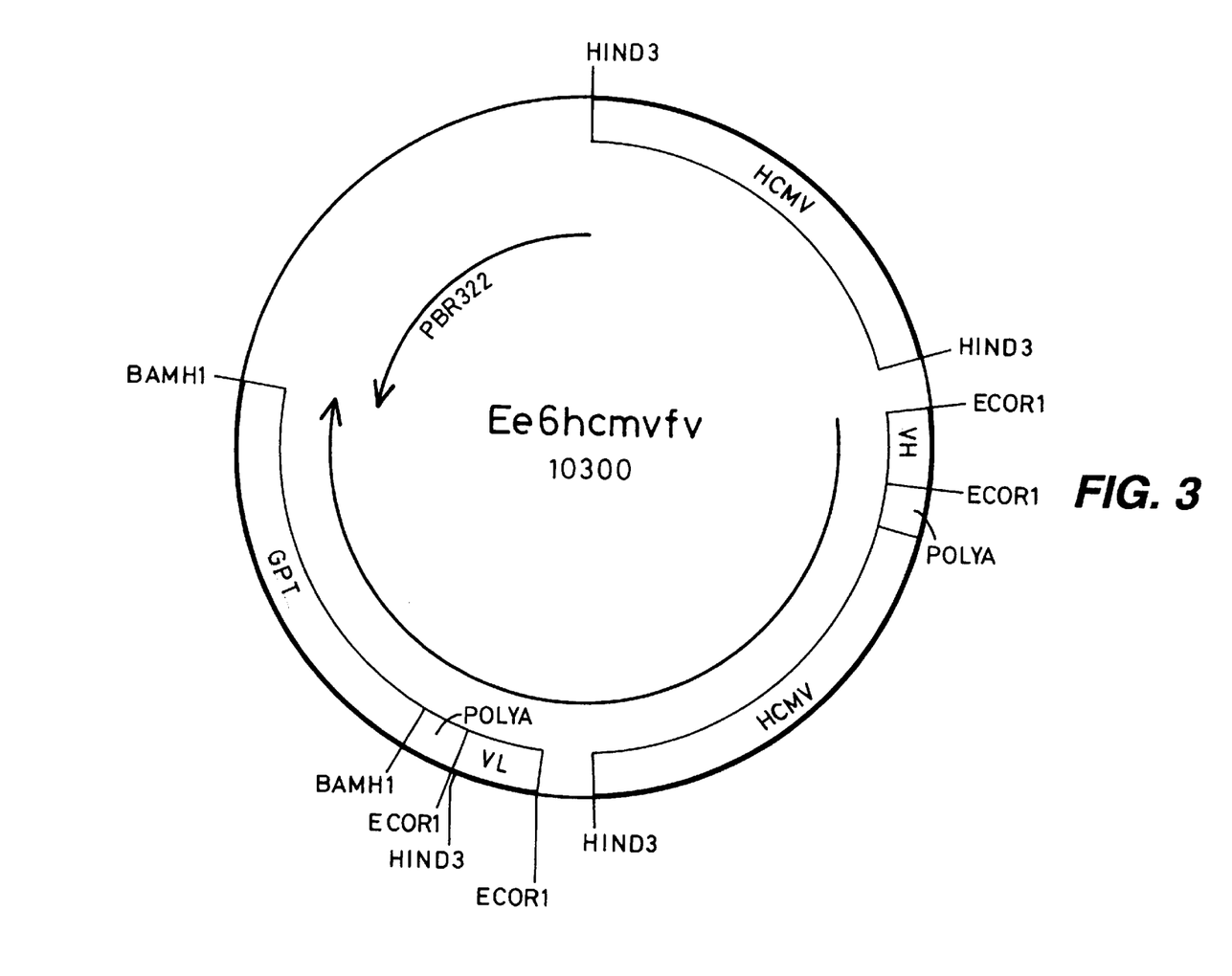
FIG. 3 shows the construction of a vector for use in producing an anti-TAG72 Fv fragment.

A "reshaped" light chain variable domain HuVLLYS and a "reshaped" heavy chain variable domain HuVLLYS (Verhoeyen et al. [7]) were each cloned as HindIII-BamHI fragments in M13. The nucleotide sequence and corresponding amino acid sequence of the reshaped HuVLLYS gene are shown in FIG. 2. At the 3' end of each coding sequence two stop codons followed by a SacI site were introduced by site directed mutagenesis.

Between the RNA start site and the translation start of the leader sequence in each gene, a HindIII site was introduced as shown in FIG. 2. The resulting variable domain genes were cloned as HindIII-BamHI fragments into a pSVgpt vector (Mulligan and Berg [14]). The vector contained a EcoRI-HindIII fragment of an Ig-heavy chain enhancer (IgHenh) as a linker (Neuberger et al. [15]). The 3' SacI-BamHI fragment of each gene was then exchanged with a SacI-BamHI fragment of the human kappa constant region (3' end $C_K$) (Hieter et al. [13]) to provide a polyadenylation signal. Into the HindIII site of each vector a HindIII fragment of the HCMV-MIE gene (Stenberg et al. [11] and Boshart et al. [12]) containing its enhancer, promoter and the first nontranslated exon (HCKV enh-pro) was cloned. The complete VL-gene (containing Ig-enhancer, HCMV-promoter, VL-coding region and polyadenylation signal) was then subcloned as an EcoRI fragment into pBGS18 (Spratt et al. [16]) and the resulting vector pBGS-HvVLLYS was cloned into the pSVgpt-HuVLLYS vector as a BamHI-fragment as shown in FIG. 1. The final plasmid pLR1 further contained the resistance genes for the drugs ampicillin ($amp^R$), kanamycin ($Kan^R$) and mycophenolic acid (Eco gpt), two col E1 origins of replication (col E1 ori) and the SV40 enhancer (SV40 enhpro). The BamHI (B), HindIII (H), EcoRI (E) and SacI (S) restriction sites used for the cloning steps are indicated.

The plasmid was transfected by electroporation (Potter et al. [17]) into the non-producer myeloma cell line (NSO Galfre et al. [18]). Transfectants were selected with mycophenolic acid (Mulligan and Berg [14]).

Pools of transfected cell clones were screened by $^{35}$S-methionine incorporation, affinity purification of culture supernatants with lysozyme-Sepharose, and analysis on SDS-acrylamide gels.

The yield of secreted Fv fragments was about 100 to 1000 fold higher when the HCMV promoter was used as compared to constructs with the Ig promoter. The cloned cell line used for the preparation of Fv fragments secreted about 8 mg/l when grown in roller bottles. Thus it is possible to produce Fv fragments in myeloma cells with yields similar to recombinant versions of intact antibodies.

The Fv fragment contains two chains of about 12 kD (calculated values: 12,749 for VH and 11,875 for VL) when analysed on SDS gels. It is secreted in a functional form, as it can readily be purified from the culture supernatant with lysozyme-Sepharose. When the purified Fv fragment was investigated on an HPLC sizing column (Biozorbax GB250) in phosphate buffered saline (PBS), a single peak was observed and its retention time did not change between concentrations of 70 and 0.3 mg/l.

The Fv fragment was also analysed on native acrylamide gels at pH 7.5. The Fv fragment ran as a single band, which contained both the VH and the VL domain when analysed on SDS gels. This band was shifted on the native gel in the presence of lysozyme. The shifted band contained lysozyme and the VH and VL domains. Further, the isolated VL domain ran with a mobility different from that of the Fv fragment. The isolated VH did not run into the gel. These results strongly suggest that the predominant form of the Fv fragment at pH 7.5 is an associated VH-VL heterodimer.

Also its apparent molecular weight in ultracentrifuge sedimentation analysis was about 23.05±0.35 kD (assuming a partial specific volume of 0.73).

The formation of VH-VL heterodimers was further established by crosslinking with 3.7% formaldehyde/PBS at a protein concentration of 0.5 mg/l. Crosslinked VH-VL heterodimers of about 25 kD were formed. Such heterodimers still bound to lysozyme-Sepharose. Overloading of SDS gels with crosslinked material also made visible a small fraction (less than 5%) of slightly lower molecular weight material suggesting the formation of crosslinked VL homodimers. No higher molecular weight band for possible VH homodimers was observed.

Nevertheless the Fv fragment dissociated on native acrylamide gels at pH 4.5. The VH and the VL each formed a single band. Incubation of antibodies at low pH has been used historically to facilitate their proteolytic digestion, probably reflecting the same underlying structural change.

Also at neutral pH, when the Fv fragment is predominantly associated, it is in a dynamic equilibrium. The purified, biosynthetically labelled VH domain exchanges with the unlabelled VH domain when incubated with unlabelled VH-VL heterodimer. The labelled VH-VL heterodimers could be trapped by crosslinking with formaldehyde. The exchange is fast enough to reach an equilibrium during the overnight crosslinking procedure without a preincubation in the absence of reagent.

The type of protein produced by the method of the present invention is of potential value for both structural studies and clinical applications. Thus these Fv fragments should especially simplify the assignment of signals in NMR spectra, because the same p-sheet frameworks can be used for different antigen binding sites. For clinical applications the reuse of hypervariable regions (and thereby the specificity) in the context of new frameworks might help to overcome a primary anti-immunoglobulin response to the frameworks of the original Fv-fragment. The dissociation of Fv fragments should not cause problems in diagnostic or therapeutic applications, although crosslinking might be advantageous in some situations. The crosslinking of the VH and VL domain is possible either chemically as shown here or by the introduction of peptide linkers on the gene level, which could contain for example cysteines for the formation of inter-domain disulphide bridges.

EXAMPLE 2

The light and heavy chain genes for antibody B72.3, an antitumour monoclonal antibody (Colcher et. al. [19] and Whittle et al. [20]) were subjected to site-directed mutagenesis (Kramer et al. [21]) to introduce EcoRI restriction sites and translation stops at the 3' ends of the variable domains. In addition, to facilitate the manipulation of the variable domain gene sequences, EcoRV and HindIII sites were also incorporated into VL to match the naturally occurring PvuII and BglI sites in VH. These genes were cloned, either separately or in tandem, into an expression vector under the control of the HCMV promoter with an SV-40 polyA addition sequence. A construct with the genes arranged in tandem is shown in FIG. 2. These constructs were tested by transient expression in COS 1 cells. Synthesis and secretion of variable domains was assayed by biosynthetically labelling the transfected cells with $^{35}$S-methionine (100 $\mu$Ci/10$^6$ cells/ml for 48 hours). The cell supernatants were subjected to immunoprecipitation with antisera reacting with either VL or VH framework epitopes.

The VH/VL construct was transfected into Chinese hamster ovary (CHO) cells by electroporation.

VH and VL domains were detected in COS cell supernatants as 14 kD (cf. calculated mol. wt. of 12.6 kD) and 12 kD (cf. calculated mol. wt. of 11.8 kD) polypetides on both reducing and non-reducing SDS polyacrylamide gels. Apparently higher levels of expression of both domains were obtained from the dual VH/VL plasmid compared to the single VH or VL plasmids. VH was co-precipitated with VL from both labelled COS cell media by the antiserum specific for VL implying some degree of association of the domains. However, insufficient amounts of material were produced by the COS cells, transiently expressing the genes either separately or in tandem, to enable the function of the putative Fv fragment to be tested in an antigen-binding competition assay. Higher levels of expression are required to investigate whether the B72.3 variable domains are functionally assembled in vivo. To this end, the VH/VL single and dual plasmids have been introduced into CHO cells, which with these plasmids appear to give greater yields of recombinant antibodies than the COS cells.

Figure 4:
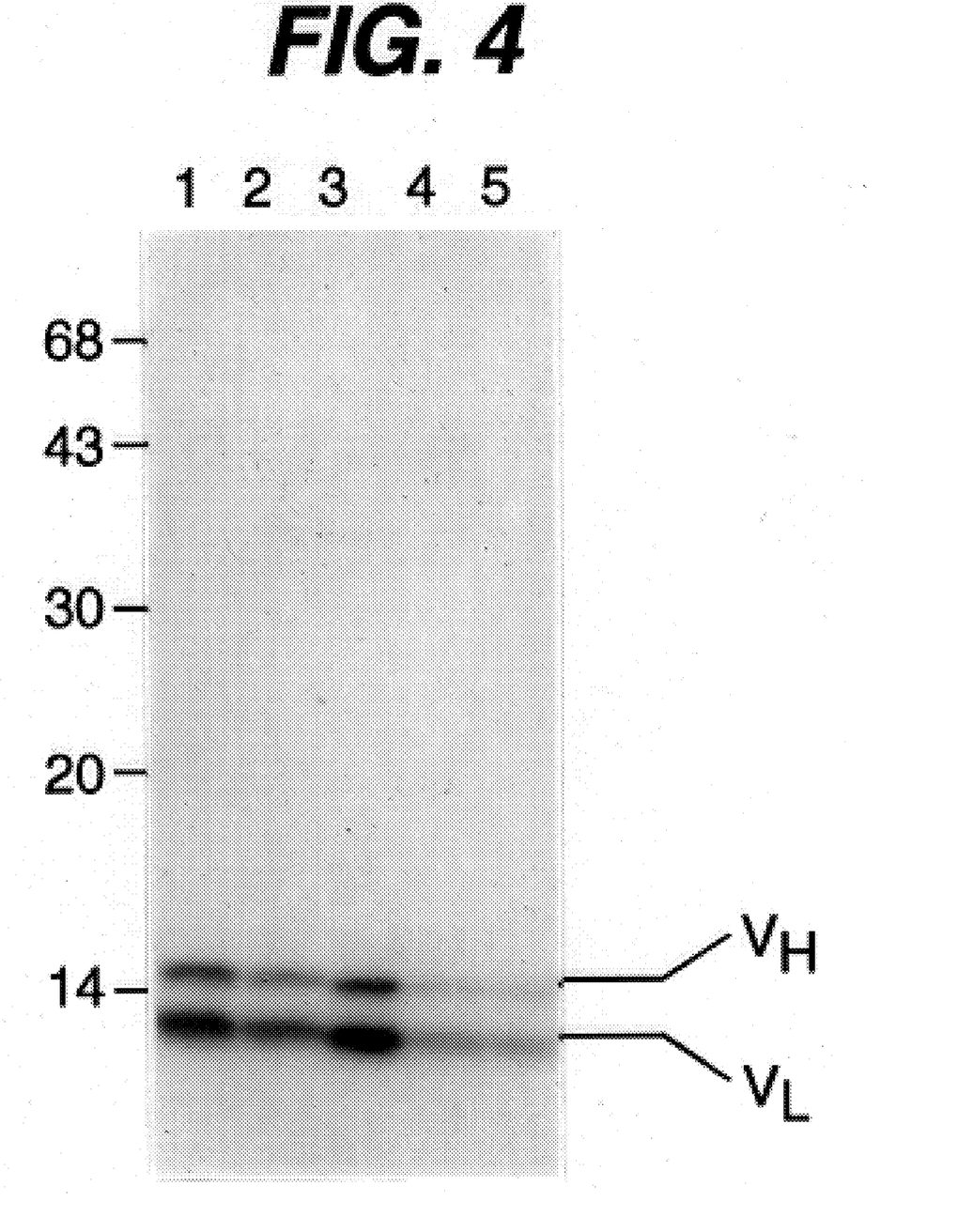
FIG. 4 shows a fluorograph of an SDS polyacrylamide gel of B72.3 Fvs.

FIG. 4 shows a fluorograph of an SDS polyacrylamide gel of B72.3 Fvs. CHO cells transfected with the vector of FIG. 1 were labelled with $^{35}$S methionine (100 μCi/ml, 48 h) and cell supernatants were subjected to immunoprecipitation using a rat antiserum specific for the B72.3 VL domain. Samples were analysed on 15% SDS polyacrylamide gels under reducing conditions. Tracks 1 to 5 show the results for five independent CHO cell lines. The numbers on the left refer to size markers.

The B72.3 Fv polypeptides were isolated from the culture supernatant of one of these cell lines (Fv3, Track 3, FIG. 4) by affinity chromatography on a mucin-Sepharose matrix. Mucin has been shown to mimic the B72.3 antigen [22]. The mucin-Sepharose used was prepared by coupling bovine submaxillary mucin to CNBr-activated Sepharose by standard techniques at 5 mg/ml of gel.

100 ml of supernatant from CHO cell line Fv3 was incubated on a roller mixer at 4° C. overnight with 1 ml of a 50% suspension of mucin-Sepharose (in 50 mM Tris, pH 8.0). The mucin-Sepharose was then recovered by pouring the incubation mix into a column. The retained mucin-Sepharose was washed with 50 mM Tris pH 8.0 until no absorbance was seen at 280 nm in the eluent from the column. Fv was then eluted with 1 ml of 0.1M citric acid. The pH of the acid eluent was then adjusted to 5.5 and assayed for antigen binding activity by ELISA.

Samples were serially diluted in microtitre plates coated with 5 μg ml bovine submaxillary gland mucin and incubated for 50 h at 4° C. After washing with phosphate buffered saline, pH 7.2, containing 0.2% Tween 20, 100 μl of a rabbit polyclonal antiserum raised to B72.3 (Fab')$_2$ was added to each well at a dilution of 1 in 2,000. This antiserum contains antibodies that recognise both B72.3 VH and VL and chains. The plates were incubated for 1 h at room temperature, washed again and 100 μl goat anti-rabbit IgG Fc-horse radish peroxidase conjugate added to each well at a dilution of 1 in 5,000.

After a further 1 h incubation at room temperature, the plates were washed again and bound antibody visualised by adding TMB substrate and reading optical density of the samples at 605 nm. The results showed that the CHO Fv3 supernatant sample was capable of binding the solid-phase mucin in this assay.

It is by no means certain that the hydrophobic interactions which are involved in the association of VH and VL will be strong enough to maintain the FV fragment in an assembled state. Further modifications of the domains may therefore be necessary to enhance or stabilise the Fv fragment. For example, this may be achieved by the introduction of covalent linkages, such as disulphides.

It will be appreciated by the skilled man that the embodiments set out above have been described by way of illustration only and that variations of detail can be made without departing from the scope of the present invention.

List of References

[1] Moore and Zaffaroni, U.S. Pat. No. 4 642 334.
[2] Field et al., "Vaccines '88", Cold Spring Harbor Publications, 1988.
[3] Skerra and Pluckthun, Science, 240, 1038–1041, 1988.
[4] Ladner and Bird, WO 88/01649.
[5] Reichmann et al., Nature, 332, 323–324, 1988.
[6] Maniatis et al., Molecular Cloning: A Laboratory Manual, Cold Spring Harbor Laboratory, Cold Spring Harbor, New York, 1982.
[7] Verhoeyen et al., Science, 239, 1534–1539, 1988.
[8] Saul, et al., J. Biol. Chem., 253, 585, 1978.
[9] Kabat, et al., Sequences of Proteins of Immunological Interest, US Department of Health and Human Serices, 1987.
[10] Epp, et al., Eur. J. Biochem., 45, 513, 1974.
[11] Stenberg, et al., J. Virol., 49, 190, 1984.
[12] Boshart, et al., Cell, 41, 521, 1985.
[13] Hieter, et al., Cell, 22, 197, 1980.
[14] Mulligan, and Berg et al., PNAS-USA, 78, 2072, 1981.
[15] Neuberger et al. Nature, 314, 268–270, 1985.
[16] Spratt, et al., Gene, 41, 337, 1986.
[17] Potter, et al., PNAS-USA, 81, 7161, 1984.
[18] Galfre, et al., Meth. Enzymol., 73, 1, 1981.
[19] Colcher, et al., PNAS-USA, 78, 3199, 1981.
[20] Whittle, et al., Protein Engineering, 1, 499, 1987.
[21] Kramer, et al., Nuc. Acids Res., 12, 9441, 1984.
[22] Kjeldsen et al., Cancer Res., 48, 2214, 1988.

We claim:

1. A method for producing Fv fragments comprising:
   (a) providing a first transcription unit which encodes a signal sequence 5' to a first DNA and operatively linked to said first DNA, and wherein said first DNA encodes the variable domain only of an antibody heavy chain;
   (b) providing a second transcription unit which encodes a signal sequence 5' to a second DNA and operatively linked to said second DNA, and wherein said second DNA encodes the variable domain only of an antibody light chain, said light chain variable domain being complementary to the heavy chain variable domain;
   (c) inserting the first transcription unit into a first eukaryotic expression vector;
   (d) inserting the second transcription unit into a second eukaryotic expression vector;
   (e) transforming a eukaryotic host cell with both the first and second expression vectors; and
   (f) culturing the transformed host cell under conditions which cause the heavy and light chain variable domains to be synthesized, correctly assembled and secreted by the host cell such that functional Fv fragments are produced in the culture supernatant.

2. The method of claim 1, wherein one of both of the variable domains is expressed as a fusion protein comprising an effector protein selected from the group consisting of an enzyme, ligand and toxin, wherein the effector protein is fused to the C-terminal end of the variable domain.

3. The method of claim 1, wherein the DNAs encoding the heavy and light chain variable domains are altered toward their 3' ends so that one or more cysteine residues are incorporated towards the C-terminal end of each variable domain.

4. The method of claim 1, wherein the DNAs coding for the signal sequences and variable domains are derived from DNAs encoding for a monoclonal antibody.

5. A method for producing Fv fragments comprising:
   (a) providing a first transcription unit which encodes a signal sequence 5' to a first DNA and operatively linked to said first DNA, wherein said first DNA encodes the variable domain only of an antibody heavy chain;
   (b) providing a second transcription unit which encodes a signal sequence 5' to a second DNA and operatively linked to said second DNA, wherein said second DNA encodes the variable domain only of an antibody light chain, the light chain variable domain being complementary to the heavy chain variable domain;
   (c) inserting the first transcription unit into a eukaryotic expression vector;
   (d) inserting the second transcription unit into said eukaryotic expression vector;

(e) transforming a eukaryotic host cell with the eukaryotic expression vector containing both the first and second transcription units; and, (f) culturing the transformed host cell under conditions which cause the heavy and light chain variable domains to be synthesized, correctly assembled and secreted by the host cell such that functional Fv fragments are produced in the culture supernatant.

6. The method of claim 5, wherein one of both of the variable domains is expressed as a fusion protein comprising an effector protein selected from the group consisting of an enzyme, ligand and toxin, wherein the effector protein is fused to the C-terminal end of the variable domain.

7. The method of claim 5, wherein the DNAs encoding the heavy and light chain variable domains are altered toward their 3' ends so that one or more cysteine residues are incorporated towards the C-terminal end of each variable domain.

8. The method of claim 5, wherein the DNAs coding for the signal sequences and variable domains are derived from DNAs encoding for a monoclonal antibody.

9. A method for producing Fv fragments comprising:

providing a first eukaryotic expression vector which comprises a signal sequence 5' to a first DNA and operatively linked to said first DNA, wherein said first DNA sequence encodes the variable domain only of an antibody heavy chain;

providing a second eukaryotic expression vector which comprises a signal sequence 5' to a second DNA and operatively linked to said second DNA, wherein said second DNA encodes the variable domain only of an antibody light chain, said light chain variable domain being complementary to the heavy chain variable domain;

transforming a eukaryotic host cell with both the first and second expression vectors; and culturing the transformed host cell under conditions which cause the heavy and light chain variable domains to be synthesized, correctly assembled and secreted by the host cell, such that functional Fv fragments are produced in the culture supernatant.

10. A method for producing Fv fragments comprising the steps:

(a) providing a eukaryotic expression vector which comprises:

a signal sequence 5' to a first DNA and operatively linked to said first DNA, wherein said first DNA encodes the variable domain only of an antibody heavy chain; and a signal sequence 5' to a second DNA and operatively linked to said second DNA, wherein said second DNA encodes the variable domain only of an antibody light chain, said light chain variable domain being complementary to said heavy chain variable domain;

(b) transforming a eukaryotic host cell with said eukaryotic expression vector; and, (c) culturing the transformed host cell under conditions which cause the heavy and light chain variable domains encoded by said vector to be synthesized, correctly assembled and secreted by the host cell, such that functional Fv fragments are produced in the culture supernatant.

* * * * *